United States Patent [19]

Kobayashi et al.

[11] Patent Number: 5,021,605

[45] Date of Patent: Jun. 4, 1991

[54] TRIFLUOROBENZENE COMPOUNDS

[75] Inventors: Hiroshi Kobayashi, Fukuoka; Masaaki Shimizu, Kanagawa, both of Japan

[73] Assignee: SDS Biotech K.K., Tokyo, Japan

[21] Appl. No.: 449,220

[22] Filed: Dec. 12, 1989

Related U.S. Application Data

[62] Division of Ser. No. 243,753, Sep. 14, 1988, Pat. No. 4,925,966.

[30] Foreign Application Priority Data

Sep. 14, 1987 [JP] Japan ................................ 62-228286

[51] Int. Cl.$^5$ ........................................... C07C 255/51
[52] U.S. Cl. .................................... 558/425; 558/419
[58] Field of Search ......................................... 558/425

[56] References Cited

FOREIGN PATENT DOCUMENTS 0023358 2/1985 Japan .
2165239 4/1986 United Kingdom .

OTHER PUBLICATIONS

Chemical Abstracts vol. 75(1971), abst. No. 109073a. Journal of the Chemical Society, Part II, 1965, pp. 2658-2661, Aroskar et al.

*Primary Examiner*—Joseph Paul Brust
*Assistant Examiner*—Jacqueline Haley
*Attorney, Agent, or Firm*—Sughrue, Mion, Zinn, Macpeak & Seas

[57] ABSTRACT

A trifluorobenzene compound represented by the general formula (I):

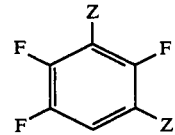

wherein Z represents a cyano group or a carboxyl group, and a process for producing said compounds.

1 Claim, No Drawings

TRIFLUOROBENZENE COMPOUNDS

This is a divisional of application Ser. No. 07/243,753 filed Sept. 14, 1988, now U.S. Pat. No. 4,925,966.

FIELD OF THE INVENTION

The present invention relates to trifluorobenzene compounds represented by the general formula (I):

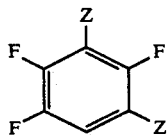

wherein Z represents a cyano group or a carboxyl group and a process for producing said compounds The trifluorobenzene compounds having the general formula (I) are novel compounds which have not been described in any of the previously published documents. These compounds are useful as starting materials for the manufacture of medicines, agrichemicals and other industrial chemicals. For instance, 2,4,5-trifluorobenzoic acid which is an intermediate for the synthesis of fluorine-containing 4-pyridone-3-carboxylic acid based bactericides can be produced by a sequence of steps starting with the compounds of the present invention.

BACKGROUND OF THE INVENTION

Several methods have been known for producing 2,4,5-trifluorobenzoic acid from 2,4,5-trifluorobromobenzene, such as synthesis by Grignard reactions as described, for example, in JP-A-58-188839 (The term "JP-A" as used herein means an "unexamined published Japanese patent application") and synthesis by reaction with cuprous cyanide as described, for example, in JP-A-60-72885, but these methods suffer disadvantages such as difficulty involved in obtaining 2,4,5-trifluorobromobenzene as a starting material.

Many reactions have also been known for dehalogenating aromatic halogen compounds with reducing agents and they include, for example, reduction with triethylsilane in the presence of palladium on carbon as described in J. Org. Chem., 34, G38 (1969), reduction with a zinc/acetic acid system as described in Organic Synthesis, Coll. Vol. 5, p.149 (1973), reduction with a copper/benzoic acid system as described in J. Amer. Chem. Soc., 75, 3602 (1953), and reduction with a triethylsilane/cyclohexane system under ultraviolet irradiation as described in Synthesis, 1971, 537. However, the process of the present invention is not disclosed in any of the known documents including those listed above. The major problem with the prior art methods concerns the need to selectively reduce the 4-position only of tetrafluoroisophthalonitrile which contains four possible sites of dehalogenation (defluorination). It should also be mentioned that 2,4,5-trifluoroisophthalonitrile and 2,4,5-trifluoroisophthalic acid are novel compounds and processes for producing them are of course not yet to be known.

SUMMARY OF THE INVENTION

The main object, therefore, of the present invention is to provide a compound that is useful as a starting material for the synthesis of 2,4,5-trifluorobenzoic acid. In one aspect, the present invention intends to provide a process by which a novel compound 2,4,5-trifluoroisophthalonitrile can be produced selectively by reacting tetrafluoroisophthalonitrile with a metal hydride. In another aspect, the present invention aims at providing a process for producing a novel compound 2,4,5-trifluoroisophthalic acid with high yield by hydrolyzing 2,4,5-trifluoroisophthalonitrile under acidic conditions. In a further aspect, the present invention provides the compounds produced by these processes.

The present inventors conducted intensive studies on the reaction of tetrafluoroisophthalonitrile with metal hydrides. As a result, they found a process for producing 2,4,5-trifluoroisophthalonitrile which comprises reacting tetrafluoroisophthalonitrile with a metal hydride at −80 to 100° C. in an aprotic solvent. The 2,4,5-trifluoroisophthalonitrile produced by this process is a novel compound. The present inventors also conducted studies on the reaction of hydrolysis of 2,4,5-trifluoroisophthalonitrile, and found a process for producing 2,4,5trifluoroisophthalic acid which comprises hydrolyzing 2,4,5-trifluoroisophthalonitrile under acidic conditions. The 2,4,5-trifluoroisophthalic acid produced by this process is also a novel compound.

DETAILED DESCRIPTION OF THE INVENTION

Tetrafluoroisophthalonitrile is used as the starting material in the process of the present invention for producing 2,4,5-trifluoroisophthalonitrile. This starting material can be prepared by known methods as described, for example, in British Patent No. 1,026,290 (1966); Bull. Chem. Soc. Japan, 40, 688 (1966); Kagaku Kogyo Zasshi, 73, 447 (1970); and JP-B-41-11368 (The term "JP-B" as used herein means an "examined Japanese patent publication"). For instance, the tetrafluoroisophthalonitrile can be obtained by a reaction of potassium fluoride and tetrachloroisophthalonitrile which is the effective ingredient of a commercially available agricultural fungicide, Daconil (product of SDS Biotech K.K.).

The term "metal hydride" as used herein means both hydrogenated metal compounds and metal-hydrogen complex compounds. Useful metal hydrides include hydrides of boron, aluminum, silicon, tin, etc., lithium aluminium hydride, sodium borohydride and hydrogenated organoaluminum. Typical examples of hydrides of silicon include trimethylsilane, triethylsilane, diphenylsilane, phenylsilane, polymethyl hydroxysiloxane, etc. Typical examples of hydrides of tin include hydrogenated tri-n-butyltin, hydrogenated diphenyltin, hydrogenated di-n-butyltin, hydrogenated triethyltin, hydrogenated trimethyltin, etc. Typical examples of hydrides of aluminum include hydrogenated diisobutylaluminum, etc. Preferred examples of metal hydrides are sodium borohydride and hydrides of boron. The amount of metal hydrides used in the present invention varies with several factors including the type of metal hydrides, the reaction temperature, the reaction time and the like. Normally, metal hydrides are used in amounts of 1.1–3.0 equivalents in terms of hydrogen anion per mole of tetrafluoroisophthalonitrile, with the range of 1.3–2.5 equivalents being preferred. The higher the reaction temperature, the less of the metal hydride needs to be used.

The reaction temperature generally ranges from −80° C. to 100° C., preferably form −70° C. to 40° C. A more advantageous reaction temperature is within the range of from −70° C. to 20° C. Generally speaking, the selectivity of reaction tends to increase with decreasing temperature and more resinous by-products are prone to occur at elevated temperature.

Aprotic solvents are used as reaction solvents in the present invention. Typical examples of the aprotic solvents include ethyl ether, benzene, toluene, xylene, cyclohexane, tetrahydrofuran, dioxane, dimethyl sulfoxide, acetonitrile, hexamethylphosphoramide, etc. These aprotic solvents can be used either individually or in combination. When sodium borohydride is to be used as a metal hydride, tetrahydrofuran and acetonitrile are preferred as a solvent. The amount of the aprotic solvent used in the present invention varies with several factors including the type of solvent, the type and amount of metal hydrides, and the like. Preferably, the solvent is used in amounts of 0.5 to 5 l per mol of tetrafluoroisophthalonitrile. The larger the amount of solvent used, the reaction rate is more reduced. Conversely, the smaller the amount of solvent used, the generation of heat is more vigorously caused, thereby resulting in difficulty in controlling the reaction temperature.

The reaction time ranges from 0.1 to 20 hours, preferably from 0.3 to 10 hours. The higher the reaction temperature, the shorter the reaction time tends to be.

After the above reaction, a processing in which the excess or unreacted metal hydrides are decomposed may be performed. In the processing, in order to prevent the reaction system from becoming alkaline, a suitable acid such as acetic acid, formic acid, dilute sulfuric acid, dilute hydrochloric acid or aqueous ammonium chloride solution is added in a sufficient amount to maintain acidic or neutral conditions. The amount of the acid used is sufficient if it is more than the equivalents of the metal hydrides added to the reaction. The 2,4,5-trifluoroisophthalonitrile as a reaction product can be purified and isolated by extraction with an organic solvent such as hexane, cyclohexane, toluene or petroleum ether, optionally followed by fractional distillation.

The resulting 2,4,5-trifluoroisophthalonitrile may be hydrolyzed under acidic conditions to produce 2,4,5-trifluoroisophthalic acid. Mineral acids such as sulfuric acid, phosphoric acid, etc. or organic acids such as acetic acid, etc. are used to render the reaction conditions acidic and sulfuric acid is preferred. These acids can be used either individually or in combination, and are normally used in an amount of 3 parts by weight or more per one part by weight of 2,4,5-trifluoroisophthalonitrile, preferably 3 to 20 parts by weight. The acid concentration is in the range of from 5 to 80 wt%. At low acid concentrations, the reaction rate is slowed down, and at high acid concentrations, 2,4,5-trifluorophthalimide forms as a by-product. Therefore, the preferred range of acid concentration is from 50 to 70 wt%. The reaction temperature generally ranges from 100° C. to 200° C., preferably from 130° C. to 170° C. Hydrolysis under basic conditions is not suitable for the purpose of obtaining the desired 2,4,5-trifluoroisophthalic acid since the fluorine atom at 2- or 4-position will be hydrolyzed.

The present invention is now illustrated in greater detail by way of the following Examples, but it should be understood that the present invention is not deemed to be limited thereto.

EXAMPLE 1

Forty grams (0.2 moles) of tetrafluoroisophthalonitrile (hereinafter, referred to as TFIPN) was dissolved in 200 ml of tetrahydrofuran. To the solution being cooled at $-10°$ C., a suspension of 3.20 g (0.084 moles) of sodium borohydride in 200 ml of tetrahydrofuran was added in small portions under agitation at $-10°$ C. After the addition of the suspension, the resulting reaction solution was stirred at $-5$ to $0°$ C. for 3 hours and left to stand overnight at room temperature. After adding an aqueous solution of 14.3 g (0.24 moles) of acetic acid in 20 ml of water, tetrahydrofuran was distilled off under reduced pressure. The residual brown oil was continuously extracted with hot hexane, which was distilled off under reduced pressure. The residue was subjected to fractional distillation under reduced pressure, thereby obtaining 21,65 g of a fraction having a boiling point of 104° C/5 torr. The purity of the product was at least 99%.

$^1$H NMR (ppm, internal standard: tetramethylsilane, solvent: d-CHCl3):

7.81 (ddd; J=8.54Hz 7.8Hz, 5.86Hz)

$^{19}$F NMR (ppm, internal standard: $C_6F_6$, solvent: $C_6F_6$) 60.439 (ddd; 1F; J=14.65Hz, 5.85Hz, 0.49Hz) 46.975 (ddd; 1F; J=20.50Hz, 7.81Hz, 0.48Hz) 27.663 (ddd; 1F; J=20.50Hz, 14.64Hz, 8.54Hz)

IR ($cm^{-1}$; neat)

3060, 2240, 1625, 1500, 1450, 1360, 1275, 1205, 1120, 970, 905, 735, 715, 700

The above spectroscopic data show that the product obtained was 2,4,5-trifluoroisophthalonitrile.

EXAMPLE 2

20.02 g of TFIPN was dissolved in 100 ml of acetonitrile. To the solution being cooled at $-42°$ C., a solution of 1.52 g of sodium borohydride in 100 ml of acetonitrile was added dropwise for 2 hours with vigorously stirring. The resulting reaction solution yellowed. After the addition thereof, the reaction solution was stirred for 2 hours with its temperature held at $-40°$ C. Thereafter, a solution of 10.4 g of acetic acid in 20 ml of acetonitrile was added dropwise thereto with its temperature held at $-40°$ C. After removing the refrigerant, the stirring of the reaction solution was continued until its temperature became equal to room temperature. After distilling off acetonitrile under reduced pressure, the residue was dissolved in 100 ml of toluene and the solution was washed three times with 100 ml of a saturated solution of sodium chloride. The washing water used was also extracted three times with 20 ml of toluene. After drying these resulting extracts with anhydrous magnesium sulfate, the solvent was distilled off under reduced pressure to obtain an oil in an amount of 21.10 g. The oil obtained was subjected to fractional distillation under reduced pressure, thereby obtaining 14.56 g of 2,4,5-trifluoroisophthalonitrile having a boiling point of 80–90° C./0.55 torr (yield, 80%).

EXAMPLE 3

Forty grams (0.2 moles) of TFIPN was dissolved in 300 ml of tetrahydrofuran. To the solution being cooled at $-55°$ C., a suspension of 4.75 g (0.125 moles) of sodium borohydride in 100 ml of tetrahydrofuran was added in small portions with stirring at $-55°$ C. After the addition of the suspension, the reaction solution was stirred for 2 hours with its temperature held at $-40°$ C. After a solution of 15.0 g (0.25 moles) of acetic acid in 20 ml of water was added, the stirring of the reaction solution was continued until its temperature became equal to room temperature. After distilling off tetrahydrofuran under reduced pressure, the residual oil was dissolved in 400 ml of ethyl ether and the solution was washed three times with a saturated solution of sodium chloride. After, drying with anhydrous magnesium sulfate, ethyl ether was distilled off. The residue was continuously extracted with hot cyclohexane, which was subsequently distilled off under reduced pressure to obtain an oil in an amount of 33.82 g. The oil obtained was subjected to fractional distillation under reduced pressure, thereby obtaining 25.19 g of a fraction having a boiling point of 96° C./4 torr. The purity of this product was at least 99.3%. The spectroscopic data of the product was the same as that obtained in Example 1.

EXAMPLES 4 to 8

Reactions were carried out in the same manner as in Example 1 except that the reaction conditions were changes as shown in the following Table 1. The results are also shown in Table 1 below.

TABLE 1

| Example No. | TFIPN (g) | Sodium Borohydride (g) | Reaction Temperature (°C.) | Reaction Time (hr) | Products A | B | C | D |
| --- | --- | --- | --- | --- | --- | --- | --- | --- |
| 4 | 2.00 | 0.10 | 30 | 4 | 48 | 0 | 27 | 28 |
| 5 | 2.00 | 0.23 | 30 | 6 | 34 | 18 | 0 | 48 |
| 6 | 2.00 | 0.15 | 65 | 1.5 | 45 | 1 | 2 | 52 |
| 7 | 40.0 | 2.95 | −10 | 6 | 77 | 0 | 5 | 18 |
| 8 | 40.0 | 3.42 | 5 | 10 | 66 | 7 | 0 | 27 |

Notes
A: 2,4,5-trifluoroisophthalonitrile,
B: various forms of difluoroisophthalonitrile (mostly 2,5-difluoroisophthalonitrile),
C: unreacted TFIPN, and
D: products other than A, B, and C (mostly resinous materials)

EXAMPLE 9

35.4 g of 2,4,5-trifluoroisophthalonitrile was added to 150 ml of 60% sulfuric acid and the mixture was heated under reflux for 5 hours. As the reaction proceeded, crystallization occurred. After the reaction, the reaction mixture was cooled to room temperature and the crystal was separated by filtration. The filtrate was extracted 5 times with 100 ml of ethyl ether each and the crystal was dissolved in the ethyl ether extracts. The resulting ethyl ether solution was washed several times with 10 ml of a saturated solution of sodium chloride. Thereafter, sulfuric acid was removed by washing with 10 ml of a 5% $CaCl_2$ solution saturated with sodium chloride. Following another washing with 10 ml of a saturated solution of sodium chloride, the solution was dried with $MgSO_4$ and ethyl ether was distilled off. The resulting white solid was dissolved in 240 ml of hot water and heated under reflux for 1 hour in the presence of activated carbon. Thereafter, the solution was filtered while hot and the filtrate was evaporated under reduced pressure. The residual white solid was further dried with a vacuum pump. The product was obtained in an amount of 41.96 g (yield, 97%). It was easily soluble in water, alcohol or ethyl acetate, but slightly soluble in benzene or hexane.

mp. 214–216°, $^1$H NMR (ppm, internal standard: tetramethylsilane, solvent: $CD_3OD$): 7.94 (ddd; J=10.25Hz, 8.91Hz, 5.37Hz)

$^{19}$F NMR (ppm, internal standard: $C_6F_6$, solvent: $CD_3OD$): 51.440 (ddd; 1F; J=16.60Hz, 6.34Hz, 5.37Hz) 35.442 (ddd; 1F; J=21:24Hz, 8.91Hz, 5.37Hz) 22.454 (ddd; 1F; J=21.24Hz, 16.60Hz, 10.25Hz) IR (cm$^{-1}$; Nujol mull):

3600–2300 (br.), 1700 (br.),.1490, 1460, 1245, 1090, 950, 890, 800, 740.

These spectroscopic data show that the product obtained was 2,4,5-trifluoroisophthalic acid.

REFERENCE EXAMPLE

Synthesis of 2,4,5-trifluorobenzoic acid

A mixture of 2.20 g (0.01 mole) of 2,4,5-trifluoroisophthalic acid (dried under high vacuum). 1.0 ml of quinoline and 0.23 g of copper powder was heated on an oil bath at 200° C. After a while, the mixture liquefied and released a gas (ca. 280 ml by top purging). After the gas had been completely released, the liquefied mixture was cooled to room temperature, followed by addition of 15 ml of a mixture (1:1 by weight) of conc. HCl and water.

The mixture was subjected to repeated extraction with 100 ml of ethyl ether and the ethyl ether extracts were washed twice with 10 ml of 5% HCl solution that had been saturated with sodium chloride. Following drying on $MgSO_4$, ethyl ether was distilled off to obtain a crude crystal in an amount of 1.66 g. The crude crystal was dissolved in 20 ml of hot water and subjected to discoloration with activated carbon for 1 hour. The solution was filtered while hot and allowed to stand overnight at room temperature to obtain the desired pure product (m.p.: 100–101.5° C.) in an amount of 1.14 g (yield, 65% $^1$H NMR (ppm, internal standard tetramethylsilane, solvent: $CD_3OD$): 7.825 (td; 1H; J=10.49Hz, 10.01Hz, 6.34Hz) 7.250 (ddd; 1H; J=10.50Hz, 9.04Hz, 6.59Hz)

$^{19}$F NMR (ppm, internal standard: $C_6F_6$, solvent: $CD_3OD$): 53.806 (dddd; 1F; J=16.12Hz, 10.01Hz, 8.78Hz, 6.59Hz) "36.406 (ddt; 1F;J=20.99Hz, 10.50Hz, 9.04Hz, 8.79Hz) 20.660 (dddd; 1F; J=20.99Hz, 16.11Hz, 10.49Hz, 6.34Hz)

IR (cm$^{-1}$; Nujol mull): 200–2400 (br.), 1690, 1510, 1460, 1395, 340, 1295, 1265, 1220, 1200, 1155, 1070, 900, 860, 840, 760, 735cm$^{-1}$ The above spectroscopic data show that the product obtained was 2,4,5-trifluorobenzoic acid.

The present invention provides a process by which 2,4,5-trifluoroisophthalonitrile can be produced from TFIPN with high yield and selectivity. Defluorination of TFIPN potentially involves the formation of various by-products, i.e., 4,5,6-trifluoroisophthalonitrile, 2,4,6-trifluoroisophthalonitrile, 2,4-difluoroisophthalonitrile, 2,5-difluoroisophthalonitrile, 4,5-difluoroisophthalonitrile, 4,6-fluoroisophthalonitrile, 5-fluoroisophthalonitrile. A change in the nitrile group is another possibility since the reaction is performed under reducing conditions. However, the process for production of 2,4,5-trifluoroisophthalonitrile in accordance with the present invention is immune to these problems and enables selective production of 2,4,5-trifluoroisophthalonitrile.

The so obtained 2,4,5-trifluoroisophthalonitrile may be hydrolyzed under acidic conditions and this enables 2,4,5-trifluoroisophthalic acid to be produced with high yield.

By reacting the so produced 2,4,5-trifluoroisophthalic acid with a suitable reagent such as copper/quinoline, 2,4,5-trifluorobenzoic acid which is a useful intermediate for the synthesis of chemicals can be easily obtained.

While the invention has been described in detail and with reference to specific embodiments thereof, it will be apparent to one skilled in the art that various changes and modifications can be made therein without departing from the spirit and scope thereof.

What is claimed is:
1. 2,4,5-Trifluoroisophthalonitrile.

* * * * *